(12) United States Patent
Lee

(10) Patent No.: US 10,687,760 B2
(45) Date of Patent: Jun. 23, 2020

(54) COMBINED WEARABLE ELECTROCARDIOGRAM AND ELECTRONIC STETHOSCOPE

(71) Applicant: INTERNATIONAL BUSINESS MACHINES CORPORATION, Armonk, NY (US)

(72) Inventor: Kang-Wook Lee, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/199,805

(22) Filed: Nov. 26, 2018

(65) Prior Publication Data

US 2019/0090814 A1 Mar. 28, 2019

Related U.S. Application Data

(63) Continuation of application No. 15/274,574, filed on Sep. 23, 2016, now Pat. No. 10,172,556.

(51) Int. Cl.
*A61B 5/04* (2006.01)
*A61B 5/00* (2006.01)
(Continued)

(52) U.S. Cl.
CPC .......... *A61B 5/6833* (2013.01); *A61B 5/0006* (2013.01); *A61B 5/01* (2013.01);
(Continued)

(58) Field of Classification Search
CPC ....... A61B 5/6833; A61B 5/0006; A61B 5/01; A61B 5/02416; A61B 2/04085;
(Continued)

(56) References Cited

U.S. PATENT DOCUMENTS 5,807,268 A * 9/1998 Reeves ................... A61B 7/003
600/513
6,498,854 B1 12/2002 Smith
6,527,729 B1 3/2003 Turcott
(Continued)

OTHER PUBLICATIONS

Patel, S. et al., "A review of wearable sensors and systems with application in rehabilitation" Journal of Neuroengineering and Rehabilitation (Apr. 2012) pp. 1-17, vol. 9, No. 21.
(Continued)

*Primary Examiner* — Amanda K Hulbert
(74) *Attorney, Agent, or Firm* — Tutunjian & Bitetto, P.C.; Kristofer Haggerty

(57) ABSTRACT

A wearable patch system includes an electrocardiogram (ECG) sensor having electrodes configured to contact a subject. An electronic stethoscope has a diaphragm structure responsive to sounds from the subject. The ECG sensor and the electronic stethoscope are co-located to measure respective parameters concurrently from a same position. A housing is configured to support the diaphragm structure and the electrodes. The housing includes a mechanical interface configured to mount on the subject. A communications circuit is disposed on or in the housing to communicate with a remote component.

20 Claims, 9 Drawing Sheets

(51) Int. Cl.
- *A61B 5/0408* (2006.01)
- *A61B 7/04* (2006.01)
- *A61B 5/1455* (2006.01)
- *A61B 5/11* (2006.01)
- *A61B 5/01* (2006.01)
- *A61B 5/024* (2006.01)

(52) U.S. Cl.
CPC ...... *A61B 5/02416* (2013.01); *A61B 5/04085* (2013.01); *A61B 5/11* (2013.01); *A61B 5/14551* (2013.01); *A61B 5/7278* (2013.01); *A61B 7/04* (2013.01); *A61B 2562/0204* (2013.01); *A61B 2562/0209* (2013.01)

(58) Field of Classification Search
CPC ..... A61B 5/11; A61B 5/14551; A61B 5/7278; A61B 7/04; A61B 2562/0204
See application file for complete search history.

(56) References Cited

U.S. PATENT DOCUMENTS

| | | |
|---|---|---|
| 6,661,897 B2 | 12/2003 | Smith |
| 6,757,392 B1* | 6/2004 | Granzotto ............ A61B 5/0002 381/67 |
| 7,724,147 B2 | 5/2010 | Brown |
| 2004/0100376 A1 | 5/2004 | Lye et al. |
| 2006/0018487 A1 | 1/2006 | Smith |
| 2016/0100817 A1* | 4/2016 | Hussain ................... A61B 7/04 600/301 |

OTHER PUBLICATIONS

Ko, J. et al., "Wireless Sensor Networks for Healthcare" IEEE (Nov. 2010) pp. 1947-1960, vol. 93, No. 11.
List of IBM Patents or Patent Applications Treated as Related dated Nov. 26, 2018, 2 pages.

* cited by examiner

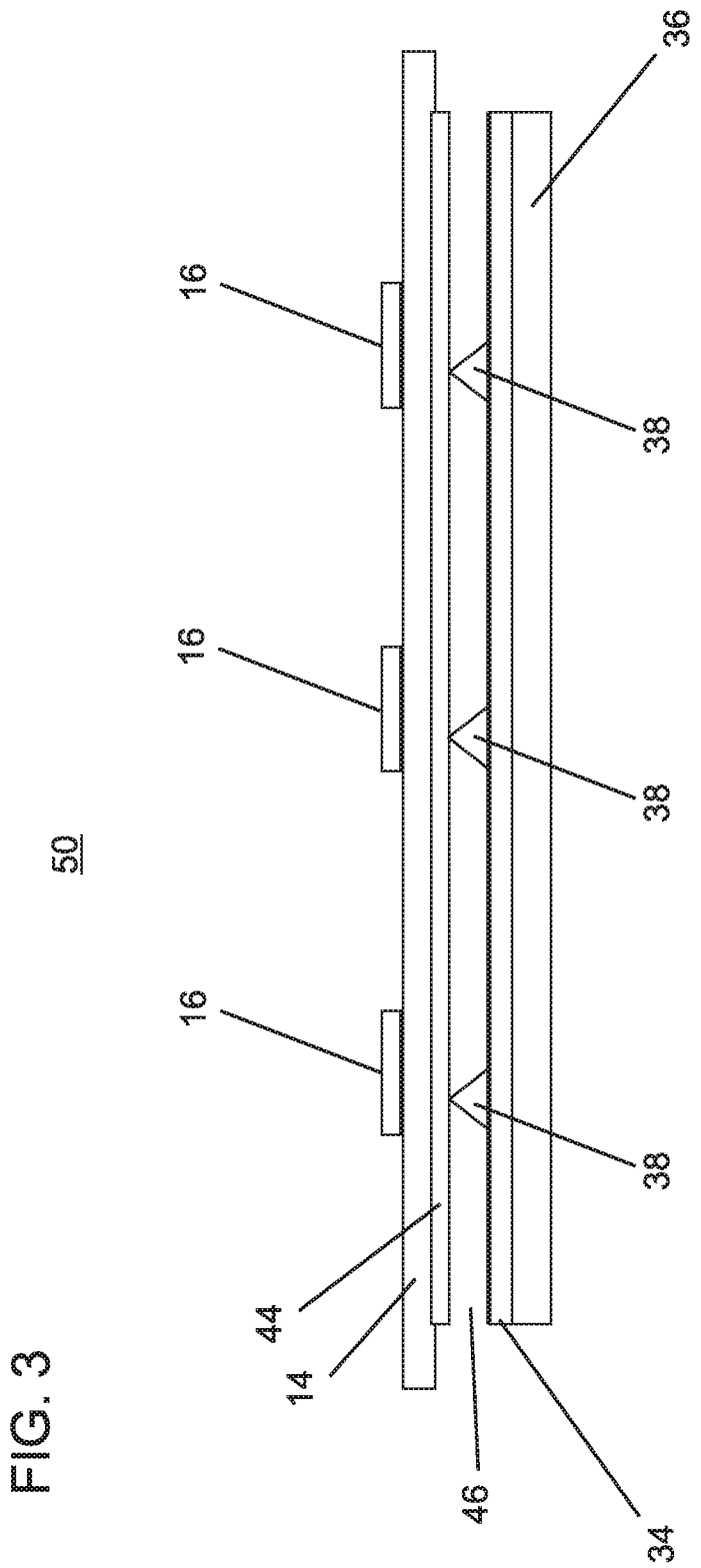

COMBINED WEARABLE ELECTROCARDIOGRAM AND ELECTRONIC STETHOSCOPE

BACKGROUND

Technical Field

The present invention generally relates to medical instruments, and more particularly to a wearable device that combines features of an electrocardiogram device and a stethoscope.

Description of the Related Art

Electrocardiogram (ECG) detects electric signals of the heart. An R wave of the ECG is known to correspond to opening an aortic valve of the heart. This opening supplies blood from the heart to the body. Depending on a person or a person's physical activity, the time of the aortic valve opening could be different from a time of a peak of the R wave. A large difference between the aortic valve opening and the time of the peak of the R wave should be known in order to determine proper heart function and other vital measurements.

SUMMARY

In accordance with an embodiment of the present invention, a wearable patch system includes an electrocardiogram (ECG) sensor having electrodes configured to contact a subject. An electronic stethoscope has a diaphragm structure responsive to sounds from the subject. The ECG sensor and the electronic stethoscope are co-located to measure respective parameters concurrently from a same position. A housing is configured to support the diaphragm structure and the electrodes. The housing includes a mechanical interface configured to mount on the subject. A communications circuit is disposed on or in the housing to communicate with a remote component.

Another wearable patch system includes an electrocardiogram (ECG) sensor having a plurality of electrodes configured to contact a subject, and an electronic stethoscope having a diaphragm structure responsive to sounds from the subject, the ECG sensor and the electronic stethoscope being co-located to measure respective parameters concurrently from a same position. A housing is configured to support the diaphragm structure and the plurality of electrodes. The housing includes a mechanical interface configured to mount on the subject. Electronic circuitry is disposed on or in the housing and includes a transceiver to conduct communications with a local hub device; a processor coupled to the transceiver to receive commands and in response to the commands make measurements of the subject; and memory coupled to the processor to store the measurements for transmission by the transceiver to the local hub.

Yet another wearable patch system includes an electrocardiogram (ECG) sensor having a plurality of electrodes configured to contact a subject; and an electronic stethoscope having a diaphragm structure responsive to sounds from the subject, the ECG sensor and the electronic stethoscope being co-located to measure respective parameters concurrently from a same position. The diaphragm structure includes a flexible diaphragm having a conductive coating forming a first conductive plate; and a second conductive plate disposed apart from the first conductive plate such that movement of the flexible dielectric diaphragm responsive to motion of the subject alters a capacitance between the first and second conductive plates. A housing is configured to support the diaphragm structure and the plurality of electrodes. The housing includes a mechanical interface configured to mount on the subject. A communications circuit is disposed on or in the housing to communicate with a remote component.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 3 is a cross-sectional view of a diaphragm device structure showing spacers between plates for measuring body sounds in accordance with an embodiment of the present invention;

DETAILED DESCRIPTION

Figure 2:
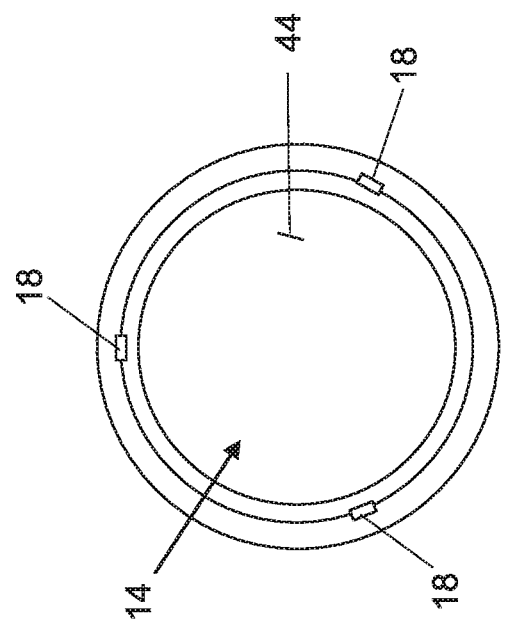
FIG. 2 is a distal view of the patch device of FIG. 1 combining an electrocardiogram device and an electronic stethoscope in accordance with an embodiment of the present invention.

In accordance with aspects of the present invention, a wearable medical device or system is provided. The wearable medical device includes a concurrent and coincident ability for an electrocardiogram (ECG) measurement and a stethoscope measurement. A single wearable patch includes ECG leads and a stethoscope diaphragm to measure heart activity, breathing cycles, blood pressure and a host of other activities concurrently and from a same physical location (i.e., at a same position and time). Other measurements and information may also be collected at the same position and time. For example, the wearable device can include a pulse oximeter (e.g., a photoplethysmogram (PPG) sensor), a gyroscope, a temperature sensor, an accelerometer, etc.

ECG detects the electric signals of the heart while PPG detects the pulse waves at various parts of body. A combination of the ECG R wave and a PPG wave at a finger or wrist can derive blood pressure using algorithms and cognitive computing. The R wave of the ECG is known to correspond to opening an aortic valve of heart. Such opening supplies blood from the heart to the body. Depending on a person or a person's physical activity, the time of the aortic valve opening may be different from the time of the peak of the R wave. If the difference is large, the accuracy of the blood pressure from the algorithms can be poor. However, this inaccuracy can be corrected by detecting heart sound signals. Placing an e-stethoscope at the same position of the ECG can provide more accurate blood pressure data, which can be subsequently corrected by the cognitive system. Placing the ECG leads and e-stethoscope at the same position on the body to take a reading can provide more health information than the case of ECG and e-stethoscope at the two separate places of the body.

The ECG leads can measure, (when also employing a wrist pulse wave sensor), blood pressure, hypertension, pulse rate, sinus block, pacemaker impulse, hypoxemia (blood oxygen level), etc. An electronic stethoscope (e-stethoscope) can monitor respiration, the heart, artery and lung conditions, etc. The e-stethoscope measures body sounds, and the measurements can be performed on the heart, lungs, digestive tract, etc. By combining the measurements and making the measurements from a common position, the combined e-stethoscope/ECG (which may also include reflective PPG (photo plethysmogram), a gyroscope, temperature sensor, etc.) can provide simplification, miniaturization, wearability, improve vital records, improve efficiency, etc. In addition, the combined e-stethoscope and ECG at the same position can provide more accurate blood pressure data, provide health information with greater depth and reduce the need for correlation of the measurements from separate devices.

In addition, the wearable device may include a motion sensing device (e.g., 9-axis accelerometer, gyroscope, and magnetometer) at the same spot of the ECG and e-stethoscope. The sensor can also provide additional health data that cannot be provided by the separate placements of the different devices since body movement in the x-y-z position can be detected by the 9-axis sensor. Then, the body movement and the ECG and e-stethoscope signals can be correlated to the movement with a cognitive computing system. Other sensor capabilities and measurements may also be provided in accordance with aspects or the present invention.

It is to be understood that aspects of the present invention will be described in terms of a given illustrative architecture; however, other architectures, structures, materials and process features and steps can be varied within the scope of aspects of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for a medical device, which may include multiple features or combinations of features. Some or all features may or may not be present on the devices in accordance with embodiments of the present invention.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

It is contemplated that one or all of the components of a medical system may be disposable, peel-pack, pre-packed sterile devices. One or all of the components of the surgical system may be reusable. The medical system may be configured as a kit with multiple sized and configured components.

It is envisioned that the present embodiments may be employed to treat disorders such as, for example, degenerative heart disease or employed for routine health evaluations. The system and methods of the present embodiments may also be employed on animals, models and other non-living substrates, such as, for example, in training, testing and demonstration.

It is to be understood that the present embodiments are not limited to the specific devices, methods, conditions or parameters described and/or shown herein, and that the terminology used herein is for the purpose of describing particular embodiments by way of example only and is not intended to be limiting. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
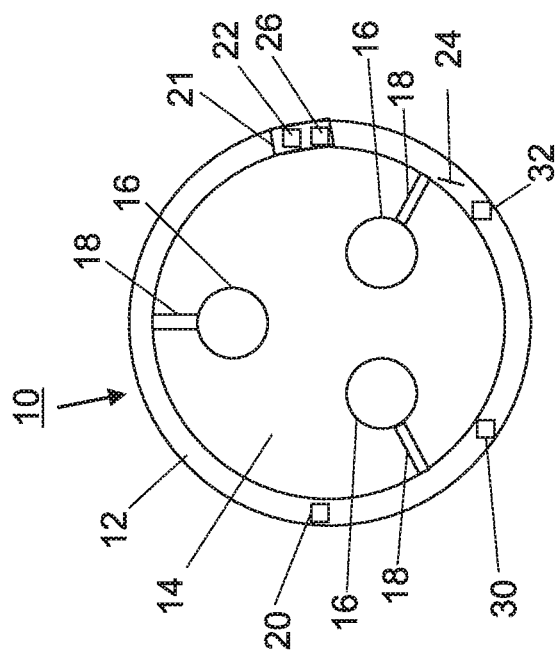
FIG. 1 is a proximal view of a patch device or system combining an electrocardiogram device and an electronic stethoscope in accordance with an embodiment of the present invention.

Referring now to the drawings in which like numerals represent the same or similar elements and initially to FIG. 1, a proximal side of a wearable patch or device 10 is illustratively shown in accordance with one embodiment. The patch 10 includes a combination of a plurality of functions. In one embodiment, at least an electrocardiogram (ECG) device is combined with an electronic stethoscope into the wearable device 10. The ECG device includes ECG leads 16 coupled to a housing 12 by connections 18. The ECG device depicted includes three leads 16; however, other numbers of leads are contemplated. The ECG leads 16 may be formed from any suitable medical grade conductive material.

The housing 12 houses electronics, batteries and other wires and circuitry needed to perform the functions of the device 10. The housing 12 also supports a diaphragm 14 employed in monitoring the heart, lungs, body motion, etc. The diaphragm 14 is coupled to the housing 12, which includes electronics to measure the displacements of the diaphragm 14. The diaphragm 14 functions with other structures to form an electronic stethoscope. The diaphragm 14 may include a dielectric material, and preferably includes a dielectric material that can be sterilized.

A surface 24 of the housing 12 interfaces with a subject (e.g., skin, etc.). The surface 24 can be an adhesive layer to provide adherence to the subject. The adhesive layer may include a replaceable adhesive to permit reuse of the device 10.

In one embodiment, housing 12 can be configured for taking a photoplethysmogram (PPG). PPG is an optically obtained volumetric measurement of an organ. A pulse oximeter 21 illuminates the skin and measures changes in light absorption to obtain the perfusion of blood in the arteries underneath the skin. The pulse oximeter 21 can be employed to perform the PPG. The pulse or body sound distends the arteries and arterioles in subcutaneous tissue. The change in volume caused by the pressure pulse is detected by illuminating the skin with a light 22 from a light-emitting diode (LED) and then the amount of light either transmitted or reflected to a photodiode 26 is measured. The pulse oximeter 21 can also be employed to monitor breathing and other circulatory conditions.

Other sensors may also be employed to further increase the richness of the collected information. In one embodiment, a motion detection sensor 30 may be employed. The motion detection sensor 30 can include a 9-axis (9 degrees of freedom) sensor or sensors configured to measure movement. Fewer axes/degrees of freedom are also contemplated. The motion detection sensor 30 can be correlated to other measurements to provide insight to anomalies in other measurements due to, e.g., body movements or other events.

In one embodiment, a temperature sensor 32 can be mounted on the housing 12 to make contact with the subject. The temperature sensor 32 measures body temperature and can do so intermittently or continually.

The patch device 10 can be on the body such as on a chest cavity or elsewhere as a wearable by using an adhesive to form a temporary attachment to the skin, integrated into a shirt or attached to a shirt, pants, socks or other clothing. The use of the ECG sensor and the e-stethoscope take advantage of being co-located on the subject. For example, when measuring a pulse transit time (PTT) using the ECG function and the e-stethoscope function, error is eliminated for the difference between the heart's electrical R signal and the heart's ventricle valve opening as the ventricle muscle squeezes blood to make the valve open. The error is limited by the co-location and concurrent measurements made by the ECG function and the e-stethoscope function.

The sensors for the ECG function and the e-stethoscope function can be co-located in close proximity at or near the heart, on the chest cavity, an arm(s), leg(s) or elsewhere on the subject.

Referring to FIG. 2, a distal side (facing away) of the wearable patch or device 10 of FIG. 1 is illustratively shown having the housing 12 and other components removed for ease of visualization of the diaphragm 14 in accordance with one embodiment. The diaphragm 14 includes a flexible or rigid dielectric material having a conductive metal coating or layer 44 formed thereon. The diaphragm 14 is free oscillate or be displaced relative to the housing 12. ECG connections 18 are shown for connecting to integrated circuits (not shown) within the housing 12. The housing 12 may include a substrate such as plastic or rubber interface portion (not shown) for the comfort of the subject. The housing 12 supports the diaphragms 14 in an operational relationship relative to the subject and other components. The housing 12 may also include circuits, chips, power supplies or other devices mounted thereon or therein. In one embodiment, a wireless communications device may be provided within the device 10 to communicate with a network and cognitive computing system.

Referring to FIG. 3, a partial side view with housing 12 removed is depicted to show an operational relationship between the diaphragm 14 and a substrate 36 in a diaphragm device structure 50. Diaphragm 14 includes the conductive material 44 formed thereon. Substrate 36 includes the conductive layer 34 on a back surface thereof. The conductive layers 34 and 44 are spaced apart by a distance or gap 46 of, e.g., about 20 microns or less, to form a capacitive device. The conductive layers 34 and 44 can include any suitable conductive material, such as a metal, e.g., Au, Ag, Cu, W, Al, etc. A capacitance or voltage change can be measured between plates (e.g., conductive layers 34 and 44) in response to changes in body sounds, pulses or movements. Slight deflections between the plates 34 and 44 are measured to determine heartbeat, respiration, body movements, etc. The thickness of the diaphragm 14 can be from about 200 microns to about 250 microns while the thicknesses of the conductive layers 16 and 44 can be about 0.1 microns or less.

In one embodiment, spacers 38 are employed in the gap 46 to maintain the gap dimension between the plates 34 and 44 and prevent shorts between the plates 34 and 44. The spacers 38 may include elastic pyramids (e.g., a polymeric dielectric material or other shapes and dielectric materials), each with an apex and base. The spacers 38 may include different sizes and elasticities to adjust the response (e.g., sensitivity) of the device 10.

Figure 4:
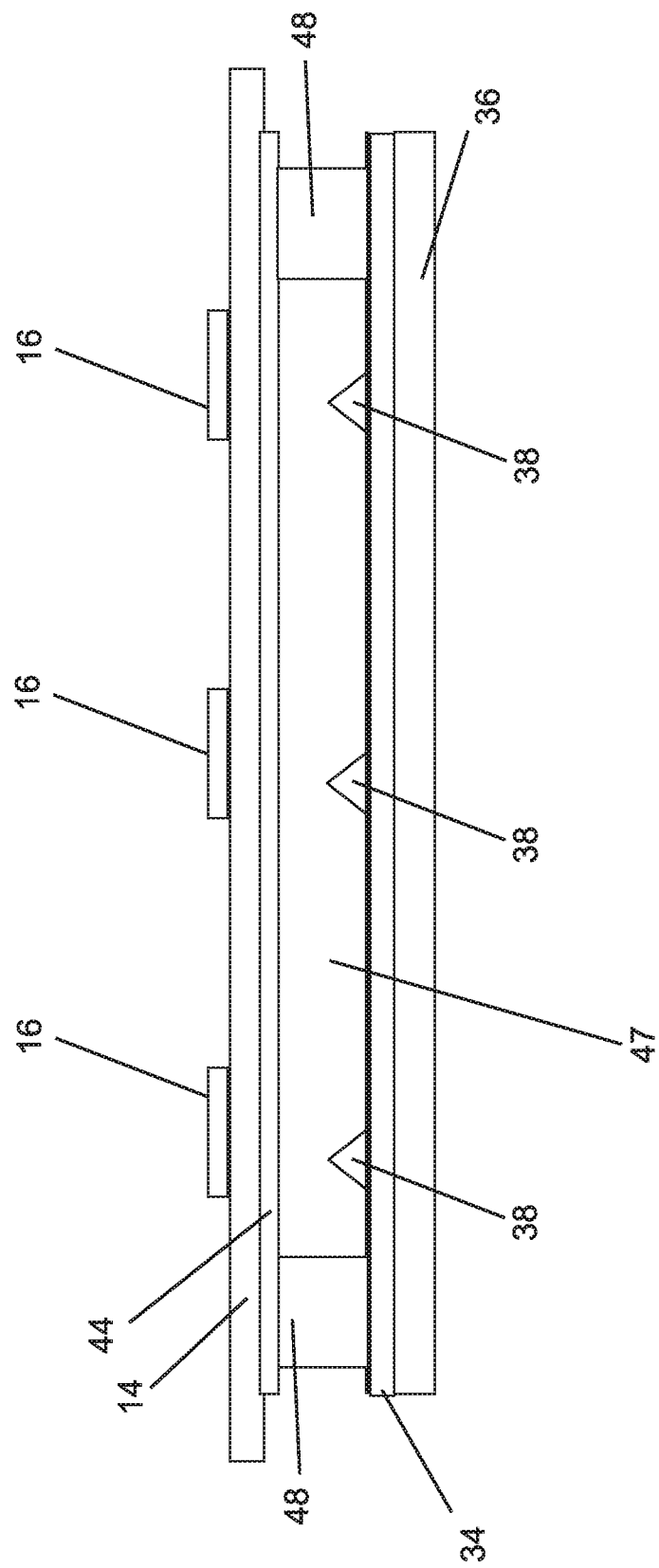
FIG. 4 is a cross-sectional view of a diaphragm device structure showing spacers between plates for measuring body sounds in accordance with another embodiment of the present invention.

Referring to FIG. 4, another partial side view with housing 12 removed is depicted to show an operational relationship between the diaphragm 14 and substrate 36 in a diaphragm device structure 60. Diaphragm 14 includes a conductive material 44 formed thereon. Substrate 36 includes the conductive layer 34 thereon. The conductive layers 34 and 44 are spaced apart by a distance or gap 47 of, e.g., about 50 microns or less, to form a capacitive device. A capacitance or voltage change can be measured between plates (e.g., conductive layers 34 and 44) in response to changes in body sounds, pulses or movements. Slight deflections between the plates 34 and 44 are measured to determine heartbeat, respiration, body movements, etc.

In one embodiment, spacers 48 are employed in the gap 47 to maintain the gap dimension between the plates 34 and 44. Spacers 38 are included to prevent shorts between the plates 34 and 44 under larger deflections. The spacers 48 may include a rigid dielectric material to provide support between the diaphragm 14 and substrate 36. The spacers 38 may include elastic pyramids (e.g., a polymeric dielectric material or other shapes and dielectric materials).

Figure 5:
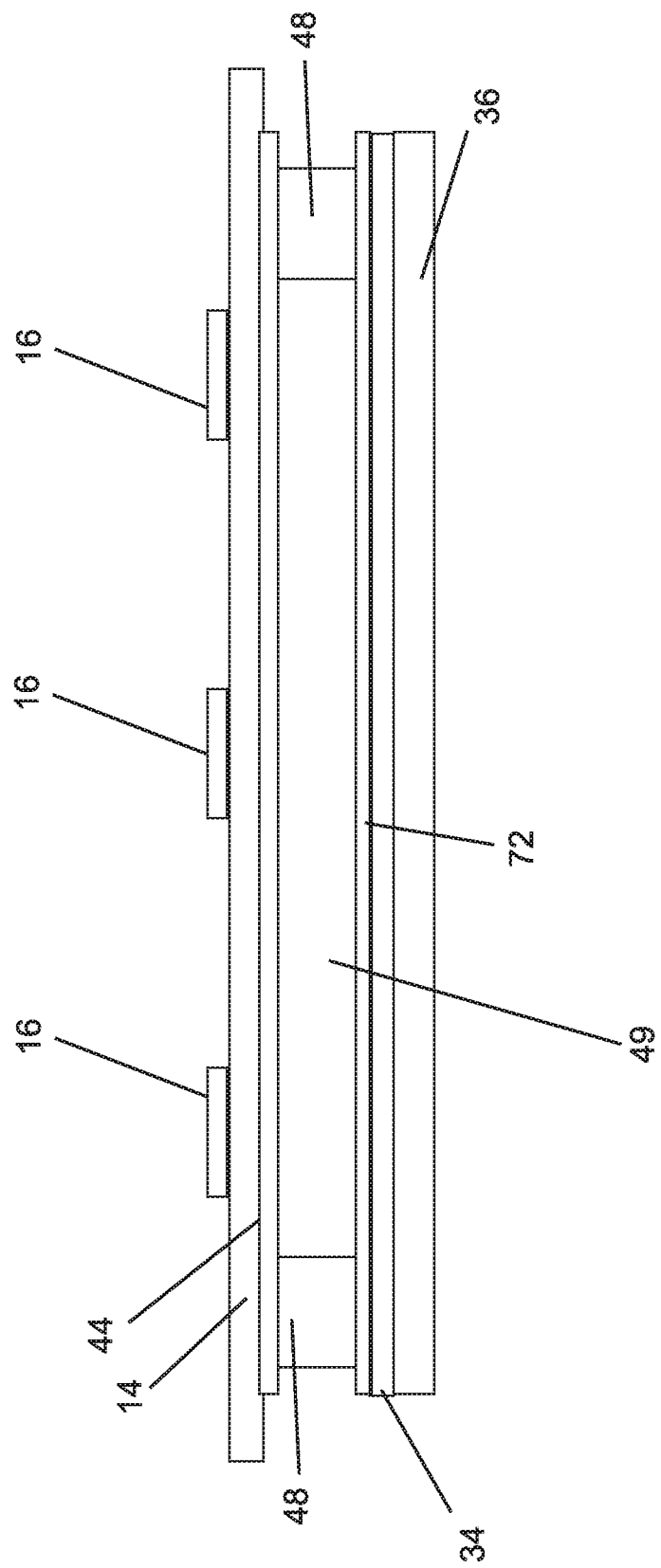
FIG. 5 is a cross-sectional view of a diaphragm device structure showing a thin layer of dielectric film on a bottom plate in accordance with another embodiment of the present invention.

Referring to FIG. 5, another partial side view with housing 12 removed is depicted to show an operational relationship between the diaphragm 14 and substrate 36 in a diaphragm device structure 70. Diaphragm 14 includes a conductive material 44 formed thereon. Substrate 36 includes the conductive layer 34 thereon. A thin dielectric layer 72 (e.g., 10-30 microns) is placed onto the conductive layer 34. The conductive layers 34 and 44 are spaced apart by a distance or gap 49 of, e.g., about 100 microns or more to form a capacitive device. A capacitance or voltage change can be measured between plates (e.g., conductive layers 34 and 44) in response to changes in body sounds, pulses or movements. Slight deflections between the plates 34 and 44 are measured to determine heartbeat, respiration, body movements, etc.

Figure 6:
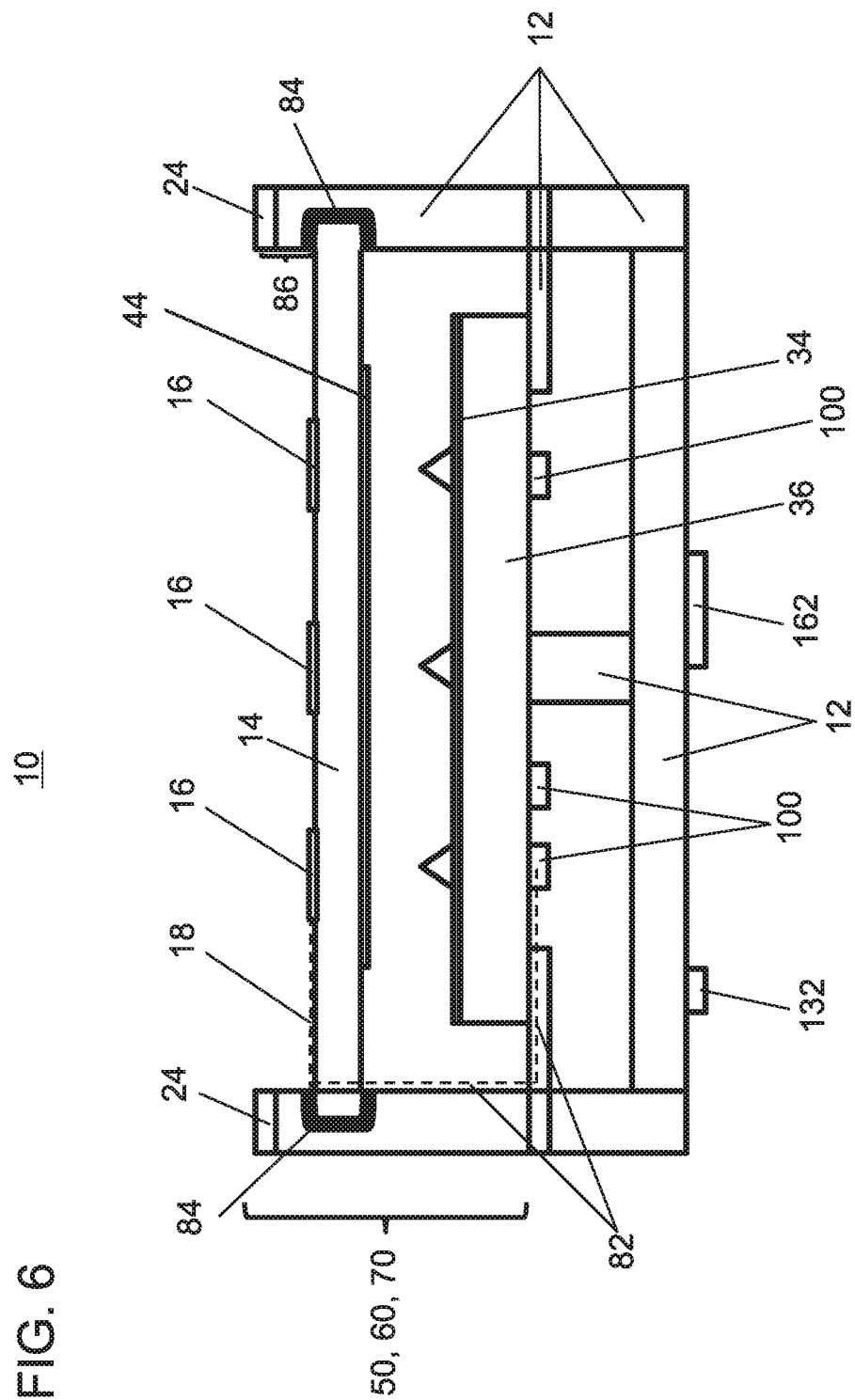
FIG. 6 is a cross-sectional view of a device showing the diaphragm device structure mounted in a housing in accordance with an embodiment of the present invention.

Referring to FIG. 6, a cross-sectional view of the device 10 is illustratively shown. The diaphragm 50 (60 or 70) is mounted within the housing 12. The housing 12 includes rim assemblies 84 for supporting the diaphragm 14 and the substrate 36 therein. The diaphragm 14 is also sealed about its periphery (e.g., using the rim assembly 84, a part of the housing 12, and the adhesive layer 24) to prevent foreign materials from entering the housing 12. Leads 18 are routed around the conductive plates 44 and 34 following a path 82 to a back of the substrate 36. The leads 18 (only one lead 18 is illustratively shown) connect to circuitry within the housing 12 to process or transmit for processing the ECG signals. The leads 18 should be shielded or placed far enough away from the conductive plates 44 and 34 to avoid cross-talk. The adhesive layer 24 can be replaced with a new adhesive layer 24 after use. A gap 86 between the surface of the diaphragm 14 and the top of the adhesive layer 24 is employed to block noise sounds from the environment so that the diaphragm 14 can respond only to the body sounds.

Circuit components (e.g., a processing system 100 and its components, such as integrated circuit chips or other devices, e.g., batteries, communication components, etc.) can be formed or mounted on the substrate 36. In one embodiment, one or more circuit boards may be mounted within the housing 12. In addition, the housing 12 can include peripheral components, such as a speaker 132, a display device 162, etc.

The device 10 preferably includes small dimensions for ease of mounting and comfort. In useful embodiments, the device is less than about 2 inches across and less than ½ inches in thickness. Other dimensions may also be employed.

Figure 7:
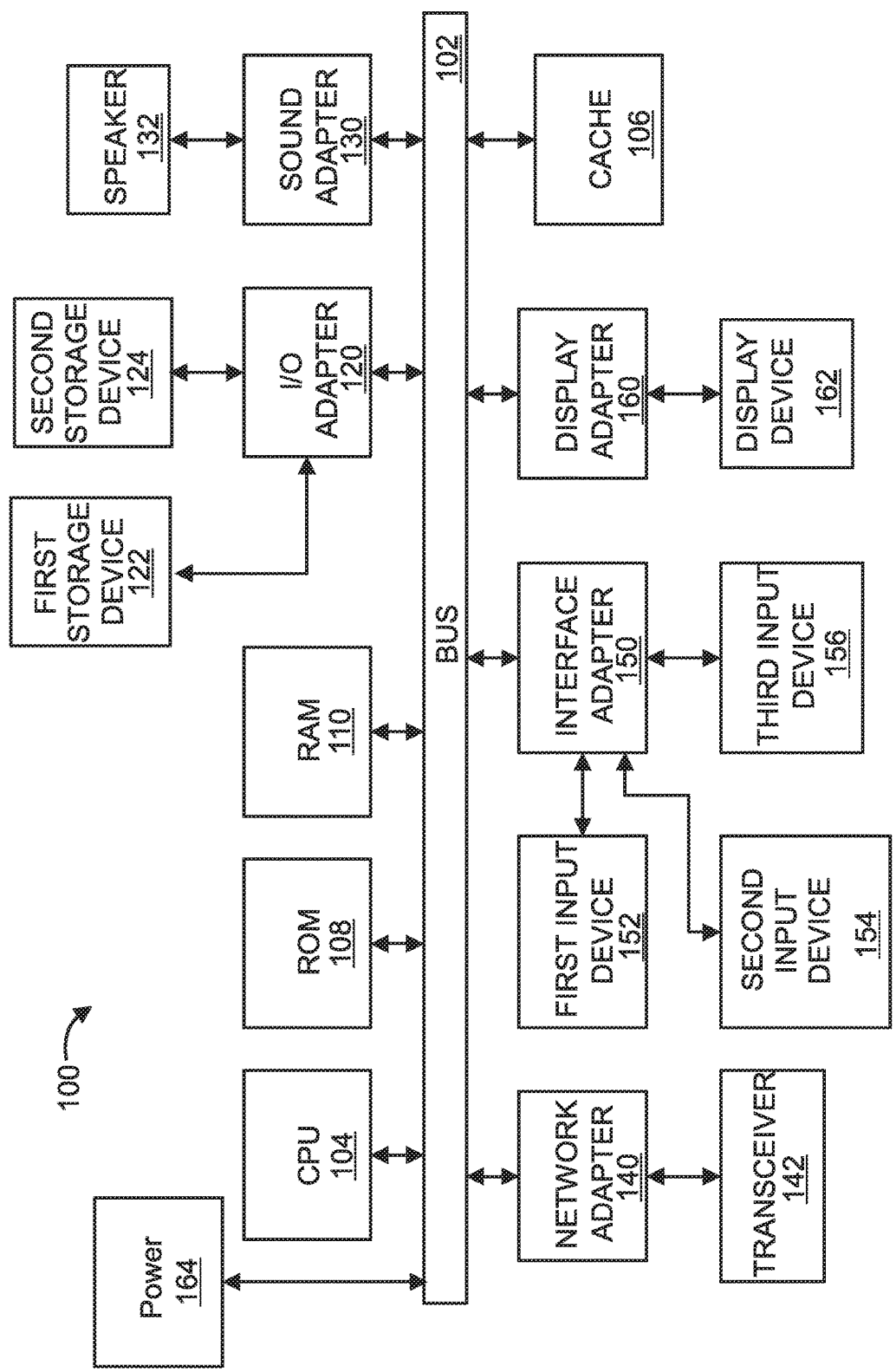
FIG. 7 is a schematic/block diagram showing an illustrative circuit/device for operating a wearable patch system in accordance with another embodiment of the present invention.

Referring to FIG. 7, an exemplary processing system 100 to which the present invention may be applied is shown in accordance with one embodiment. The processing system 100 is mounted on or in the housing 12 (FIG. 6). The processing system 100 may be integrated into one or more integrated circuits or chips and distributed within the housing 12. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a type storage device (e.g., a magnetic or optical disk, solid state storage, etc.), a solid state magnetic device, and so forth. The storage devices 122 and 124 can be the same type of storage device or different types of storage devices.

The speaker 132 is operatively coupled to system bus 102 by the sound adapter 130. A transceiver 142 is operatively coupled to system bus 102 by network adapter 140. The transceiver 142 (and associated hardware and software) may be configured to work with one or more communication protocols, such as, for example, a cellular protocol, BLUETOOTH™, an infrared protocol, etc.

The display device 162 is operatively coupled to system bus 102 by display adapter 160. The display device 162 may display a device status or setting, among other things. The display device 162 can provide feedback to a local user or permit adjustments indicated on the display device 162, e.g., a voltage adjustment, sensitivity adjustment, etc.

A first input device 152, a second input device 154, and a third input device 156 are operatively coupled to system bus 102 by interface adapter 150. The input devices 152, 154, and 156 include devices for measuring, e.g., ECG, diaphragm deflection measurements (e.g., capacitance), temperature, oximeter, motion, etc.

In one embodiment, one or more of the input devices 152, 154, and 156 can be a user interface, e.g., any of a keyboard, a mouse, a keypad, an image capture device, a motion sensing device, a microphone, a device incorporating the functionality of at least two of the preceding devices, and so forth. Of course, other types of input devices can also be used. The user input devices 152, 154, and 156 can be the same type of user input device or different types of user input devices. The user input devices 152, 154, and 156 are used to input and output information to and from system 100.

The processing system 100 includes a power source 164. The power source 164 may include a battery, rechargeable battery, an inductive rechargeable battery, a photovoltaic cell or other portable power device. The power source 164 may be scaled in accordance with the components employed.

The processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present invention provided herein.

While a number of components are depicted in FIG. 7, not all of these components are needed or desired for each embodiment. In a number of embodiments, the number of components can be scaled back to a battery, a limited processor, some memory and a transceiver for off-device communications. More components will increase the size of the device, and increase the power demands. In one embodiment, the on-device functions are reduced and recording and conditioning of data may be performed by an off-device (e.g., over a network) cognitive computing system.

The system 100 may be integrated on a chip or chips that are thin, miniaturized and low power. The system 100 may be mounted and connected within or on the housing 12 (FIG. 6). The system 100 may include software integrated within the storage devices 122, 124, cache 106, ROM 108, RAM 110, etc. The software or programs may be configured to operate inputs/sensors 152, 154, 156 and other device operations.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 8:
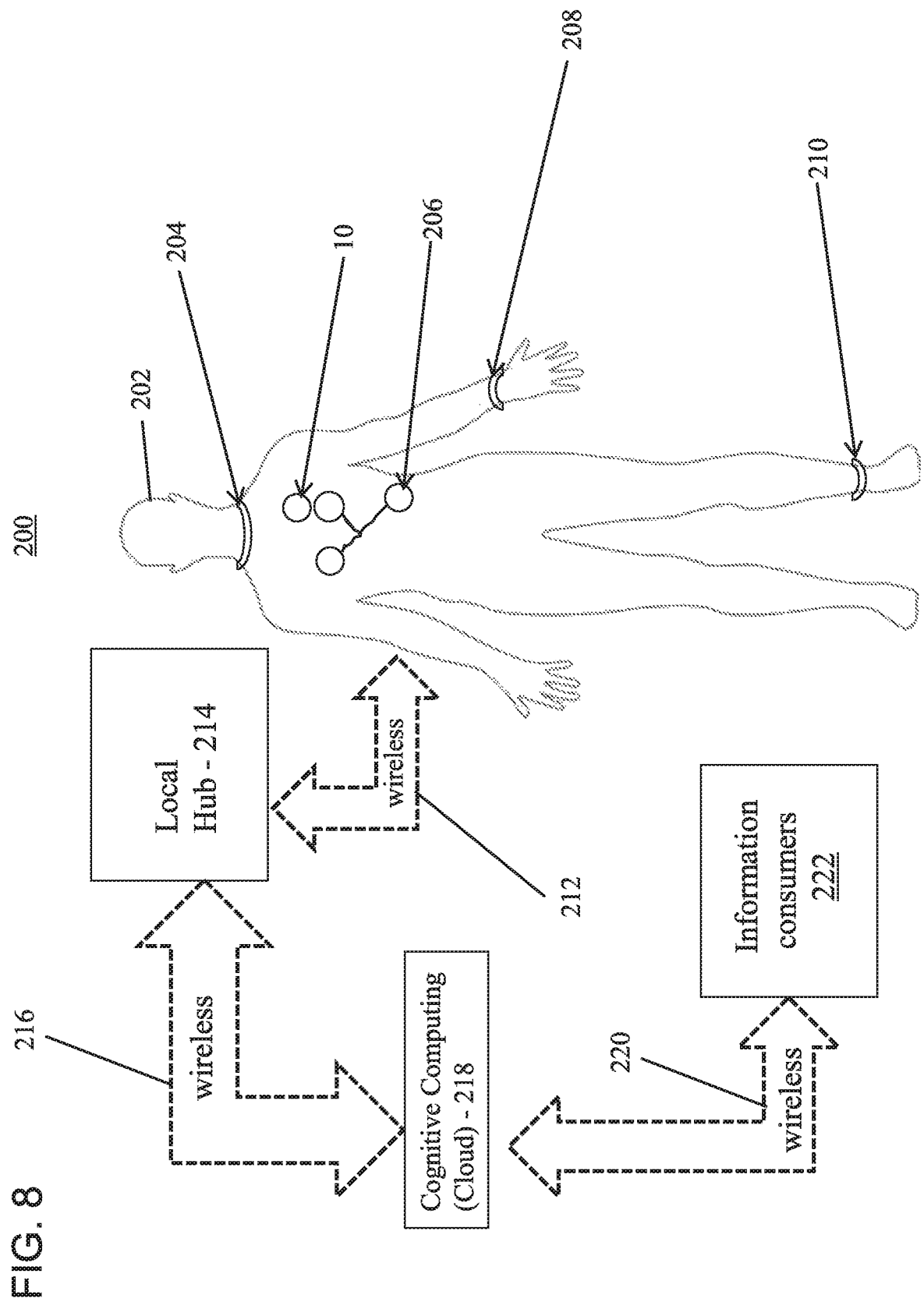
FIG. 8 is a schematic diagram showing a sensing system communicating with a networked cognitive computing system in accordance with an embodiment of the present invention.

Referring to FIG. 8, a wearable sensor system 200 is illustratively shown in accordance with one illustrative embodiment. The system 200 includes a wearable device 10, as described above. The device 10 is fixed to a subject 202. The subject 202 may have other monitoring devices connected as well. Some examples, may include, e.g., a neck pulse wave sensor 204, a wrist pulse wave sensor 208, an ankle pulse wave sensor 210, other sensors or monitors 206, etc. Some or all of these sensors may be employed to collect data from the subject 202. Some or all of these sensors may communicate with a local hub 214.

The local hub 214 may include a wireless communications device, such as a smart phone, a computer, a wireless network device (e.g. modem), etc. The local hub 214 can communicate with the transceiver 142 (FIG. 7) of device 10 by a wireless connection 212. The other sensors 204, 206, 208, 210, etc. may also employ wireless communications, if so equipped. The local hub 214 communicates with a cognitive computing system 218 over a communication link 216 (e.g., a wired or wireless communications channel). Cognitive computing system 218 may include a network server or servers configured to control, update and record measurements taken by the device 10 in accordance with embodiments of the present invention. Cognitive computing system 218 may include IBM® BLUEMIX® or the like. The cognitive computing system 218 can store the data, process the data and provide the information to consumers 222, such as e.g., doctors, hospitals, patients or other entities, over a communications link 220 (e.g., a wired or wireless communications channel).

The cognitive computing system 218 can be offered as a cloud service to compute parameters, store data, provide alerts, generate reports, etc. In one instance, pulse transit time (PTT) can be obtained between the ECG and the e-stethoscope worn on a chest of the subject as device 10. Algorithms to get obtain systolic and diastolic blood pressures in a way that the diastolic blood pressure (DBP) is dependent on the systolic blood pressure (SBP) can be computed by the cognitive computing system 218 (or in one embodiment, computed on the device 10 itself).

An algorithm for SBP, may include the algorithm of Fuke, et al. (in 35$^{th}$ Annual International Conference of the IEEE EMBS, 2013). The equation by Fuke, et al., is SBP=a*ln (1/PTT$^2$)+c where a and c are constants and ln(•) means natural logarithm. In another algorithm, a subject person's height is incorporated into the equation: SBP$_{PTT}$=a*ln(h$^2$/PTT$^2$)+b where h is a person's height and a and b are constants which can be empirically obtained and further optimized. Other parameters may also be computed by the cognitive computing system 218.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 9:
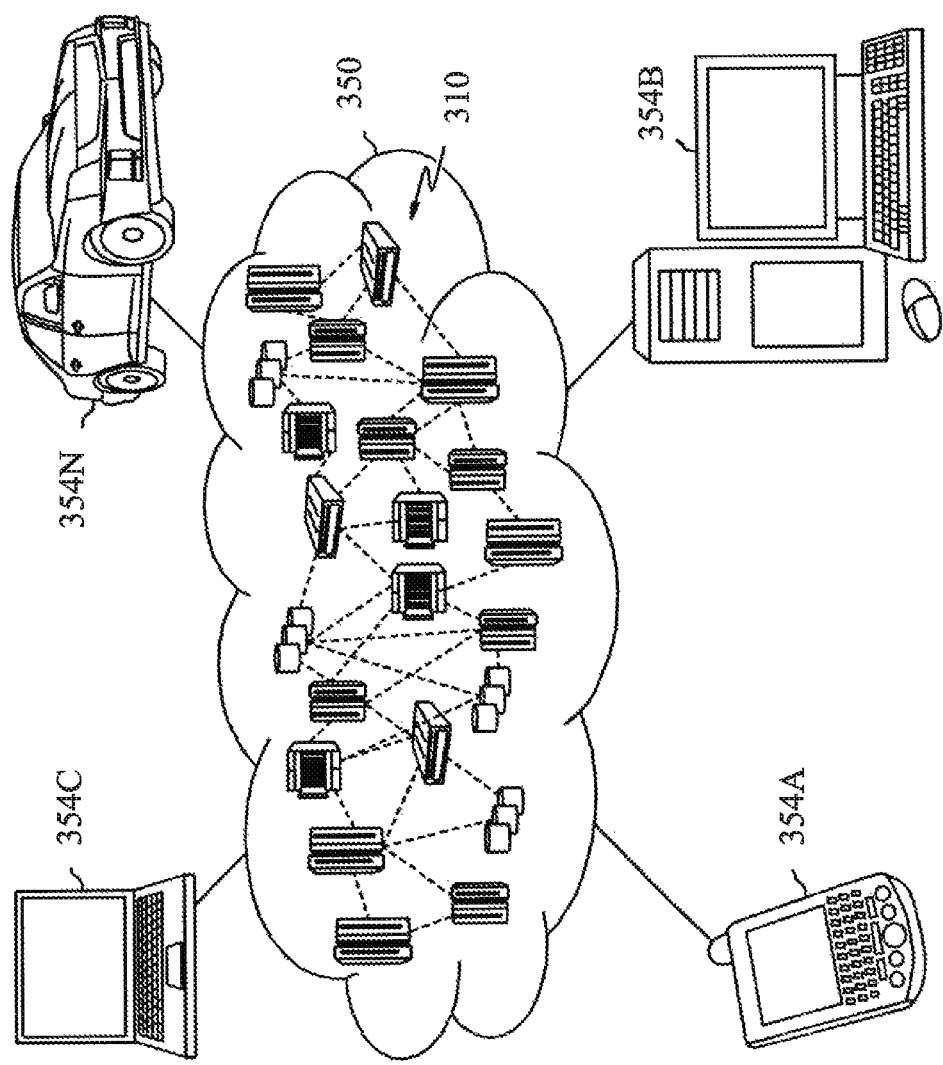
FIG. 9 is a block diagram showing an illustrative cloud computing environment in accordance with an embodiment of the present invention.

Referring to FIG. 9, an illustrative cloud computing environment 350 is depicted. As shown, cloud computing environment 350 includes one or more cloud computing nodes 310 with which local computing devices used by cloud consumers, such as, for example, devices 10, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 9 are intended to be illustrative only and that computing nodes 310 and cloud computing environment 350 can communicate with any type of computerized device over any type of network and/or network addressable connection (e.g., using a web browser).

Figure 10:
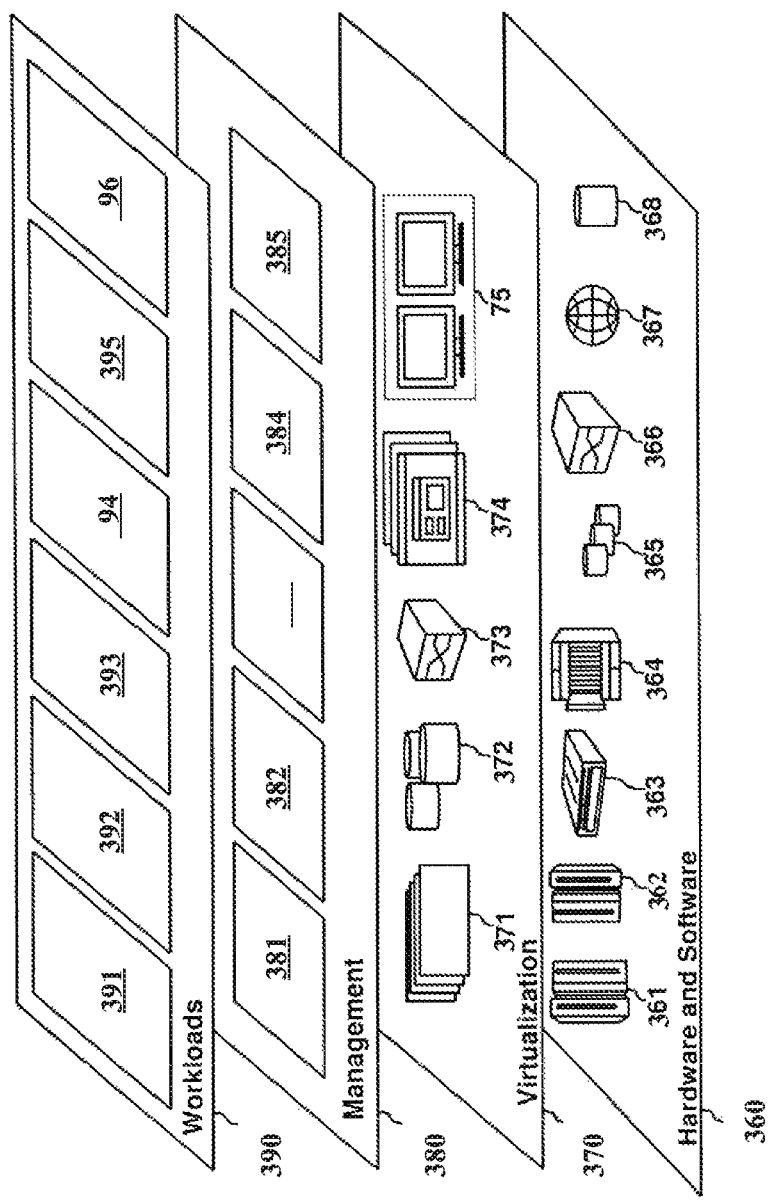
FIG. 10 is a block diagram showing a set of functional abstraction layers provided by a cloud computing environment in accordance with an embodiment of the present invention.

Referring to FIG. 10, a set of functional abstraction layers provided by cloud computing environment 350 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 360 includes hardware and software components. Examples of hardware components include: mainframes 361; RISC (Reduced Instruction Set Computer) architecture based servers 362; servers 363; blade servers 364; storage devices 365; and networks and networking components 366. In some embodiments, software components include network application server software 367 and database software 368.

Virtualization layer 370 provides an abstraction layer from which the following examples of virtual entities may be provided: virtual servers 371; virtual storage 372; virtual networks 373, including virtual private networks; virtual applications and operating systems 374; and virtual clients 375.

In one example, management layer 380 may provide the functions described below. Resource provisioning 381 provides dynamic procurement of computing resources and other resources that are utilized to perform tasks within the cloud computing environment. Metering and Pricing 382 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 383 provides access to the cloud computing environment for consumers and system administrators. Service level management 384 provides cloud computing resource allocation and management such that required service levels are met. Service Level Agreement (SLA) planning and fulfillment 385 provide pre-arrangement for, and procurement of, cloud computing resources for which a future requirement is anticipated in accordance with an SLA.

Workloads layer 390 provides examples of functionality for which the cloud computing environment may be utilized. Examples of workloads and functions which may be provided from this layer include: mapping and navigation 391; software development and lifecycle management 392; virtual classroom education delivery 393; data analytics processing 394; transaction processing 395; and a cardiovascular sensing system 396 for administering and interacting with, e.g., devices 10 having a combined wearable electrocardiogram and electronic stethoscope (FIGS. 1-6) and communicating via system 100 (FIG. 7).

Having described preferred embodiments for a combined wearable electrocardiogram and electronic stethoscope (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A wearable patch system, comprising:
an electrocardiogram (ECG) sensor having at least one electrode configured to contact a subject;
an electronic stethoscope having a diaphragm structure responsive to sounds from the subject, the at least one electrode being disposed on the diaphragm structure; and
a housing configured to support the diaphragm structure, the housing including a mechanical interface configured to mount on the subject.

2. The patch system as recited in claim 1, wherein the ECG sensor has at least two electrodes and each electrode is separated from one another and covered by the diaphragm structure when mounted on the subject.

3. The patch system as recited in claim 1, wherein the diaphragm structure includes a conductive surface that faces a second conductive surface to form a capacitive component.

4. The patch system as recited in claim 1, further comprising a pulse oximeter mounted on the housing and having a light source and a light sensor.

5. The patch system as recited in claim 1, further comprising a motion sensing device configured to measure motion of the subject.

6. The patch system as recited in claim 1, further comprising a temperature sensor configured to measure a temperature of the subject.

7. The patch system as recited in claim 1, further comprising a communications circuit includes a protocol for communicating with a local hub device to report data measured by the patch.

8. The patch system as recited in claim 1, wherein the mechanical interface includes a replaceable adhesive.

9. A wearable patch system, comprising:
an electrocardiogram (ECG) sensor having at least one electrode configured to contact a subject;
an electronic stethoscope having a diaphragm structure responsive to sounds from the subject, the at least one electrode being disposed on the diaphragm structure to measure respective parameters concurrently from a same position;
a housing configured to support the diaphragm structure, the housing including a mechanical interface configured to mount on the subject;
electronic circuitry disposed on or in the housing and including:
a transceiver to conduct communications with a local hub device;
a processor coupled to the transceiver to receive commands and in response to the commands make measurements of the subject; and
memory coupled to the processor to store the measurements for transmission by the transceiver to the local hub.

10. The patch system as recited in claim 9, wherein the ECG sensor has at least two electrodes and each electrode is separated from one another and covered by the diaphragm structure when mounted on the subject.

11. The patch system as recited in claim 9, wherein the diaphragm structure includes a conductive surface that faces a second conductive surface to form a capacitive component.

12. The patch system as recited in claim 9, further comprising a pulse oximeter mounted on the housing and having a light source and a light sensor.

13. The patch system as recited in claim 9, further comprising a motion sensing device configured to measure motion of the subject.

14. The patch system as recited in claim 9, further comprising a temperature sensor configured to measure a temperature of the subject.

15. The patch system as recited in claim 9, wherein the transceiver includes a protocol for communicating with a local hub device to report data measured by the patch.

16. The patch system as recited in claim 15, wherein the local hub device communicates with a network computer to compute cardiovascular parameters based on a plurality of measurements taken from the subject.

17. The patch system as recited in claim 9, wherein the mechanical interface includes a replaceable adhesive.

18. A wearable patch system, comprising:
an electrocardiogram (ECG) sensor having at least one electrode configured to contact a subject;
an electronic stethoscope having a diaphragm structure responsive to sounds from the subject, the at least one electrode being disposed on the diaphragm structure to measure respective parameters concurrently from a same position, wherein the diaphragm structure includes:
a flexible diaphragm having a conductive coating forming a first conductive plate; and
a second conductive plate disposed apart from the first conductive plate such that movement of the flexible dielectric diaphragm responsive to motion of the subject alters a capacitance between the first and second conductive plates; and
a housing configured to support the diaphragm structure, the housing including a mechanical interface configured to mount on the subject.

19. The patch system as recited in claim 18, wherein the first and second conductive plates are separated by spacers to prevent shorts.

20. The patch system as recited in claim 18, further comprising one or more of a pulse oximeter, a motion sensing device and/or a temperature sensor.

* * * * *